United States Patent [19]

Beck

[11] 4,166,065

[45] Aug. 28, 1979

[54] PROCESS FOR THE PREPARATION OF PERFLUOROALKANE SULFONAMIDES

[75] Inventor: Heinz Beck, Duren, Fed. Rep. of Germany

[73] Assignee: Akzona Incorporated, Asheville, N.C.

[21] Appl. No.: 942,586

[22] Filed: Sep. 15, 1978

[30] Foreign Application Priority Data

Sep. 30, 1977 [DE] Fed. Rep. of Germany ....... 2744044

[51] Int. Cl.$^2$ ............................................ C07C 143/74
[52] U.S. Cl. .................................... 260/401; 252/449; 260/556 F
[58] Field of Search ............................ 260/401, 556 F; 252/449

[56] References Cited

U.S. PATENT DOCUMENTS

| 2,732,398 | 1/1956 | Brice et al. .................. 260/556 F X |
| 2,759,019 | 8/1956 | Brown et al. ..................... 260/556 F |
| 3,231,600 | 1/1966 | Jones et al. ...................... 252/449 X |
| 3,458,571 | 7/1969 | Tokoli ............................... 260/556 F |
| 3,829,466 | 8/1974 | Staffe et al. .................. 260/556 F X |
| 3,972,926 | 8/1976 | Moore et al. ..................... 260/556 F |

*Primary Examiner*—Thomas Waltz
*Attorney, Agent, or Firm*—Francis W. Young; Robert F. Green

[57] ABSTRACT

An improved process for preparing perfluoroalkane sulfonamides by reacting a perfluoroalkane sulfonylfluoride with an amine as disclosed. The improvement comprises performing the reaction in the presence of at least about 1 mole of finely divided silica having a surface area from about 20 m$^2$/g to about 600 m$^2$/g, per mole of sulfonyl fluoride.

9 Claims, No Drawings

PROCESS FOR THE PREPARATION OF PERFLUOROALKANE SULFONAMIDES

BACKGROUND OF THE INVENTION

This invention relates to an improved process for preparing perfluoroalkane sulfonamides by reacting a perfluoroalkane sulfonylfluoride with an amine.

Perfluoroalkane sulfonamides are well known in the art. The primary use of such compounds resides mainly in the fact that they are important intermediate products in the preparation of surface-active substances.

Typically, perfluoroalkane sulfonamides are prepared by reacting perfluoroalkane sulfonylfluorides with amines. Thus, for example, U.S. Pat. No. 2,732,398 teaches the reaction of compounds such as perfluoro-n-octane sulfonylfluoride with piperidine or morpholine, whereby the corresponding sulfonamides are formed. However, in the reaction described therein, the yield of the desired product is relatively low and the product is very impure and difficult to purify.

In U.S. Pat. No. 2,759,019, in which the reaction of perfluoroalkane sulfonylfluorides with amines is also described, it is indicated that the crude reaction product which is in the form of an ethereal solution should be washed with water three times, after which, the ether layer is evaporated and the crude reaction product recrystallized twice from methyl cyclohexane. At a minimum, such complex recovery steps are burdensome, if not prohibitive.

German Pat. No. 1,275,054, corresponding essentially to U.S. Pat. No. 3,458,571, also is concerned with the reaction of perfluoroalkane sulfonylfluorides with amines. The patent recommends mixing the reaction solution with an alcoholic solution of an inorganic base and processing the reaction product in a typical manner, after removal of the precipitated inorganic fluoride. Such a method is also very expensive and requires a time consuming purification process. It is also disadvantageous that, generally, a large excess of amine must be used. Furthermore, the purification is cumbersome and results in a product which is not as pure as is typically desirable. Finally, the process results in soluble fluorine compounds which may be environmentally harmful and there is no indication with respect to how the adverse environmental pollution might be counteracted.

With respect to the reactions described in all of the above patents, there is also a danger that the forming hydrofluoric acid may corrode the reaction vessels. As perfluoroalkane sulfonamides with a high degree of purity are required for various applications, there still exists a need for an improved preparation process which will particularly result in purer products and will not present any problems with respect to the disposal of hydrofluoric acid or other fluorine compounds. Furthermore, such a process which will not result in the corrosion of reaction vessels is especially desirable.

Thus, the primary purpose of this invention is to make available a process by means of which it is possible to prepare perfluoroalkane sulfonamides of satisfactory purity by reacting perfluoroalkane sulfonylfluorides with amines, resulting in a crude reaction product which can be converted, by relatively simple methods and without large expenditures, to a purer end product. Furthermore, the desired process should require only a small excess of amine in order to obtain an approximately quantitative conversion of the perfluoroalkane sulfonylfluoride. Additionally, the desired process should allow for the relatively simple removal of the hydrofluoric acid liberated during the reaction, without resulting in any problems such as environmental pollution while at the same time preventing corrosion of the reaction vessel, even if it is made of glass.

SUMMARY OF THE INVENTION

The Applicant has now discovered an improved process for preparing perfluoroalkane sulfonamides by reacting a perfluoroalkane sulfonylfluoride with an amine. The improvement comprises performing the reaction in the presence of finely divided silica.

DESCRIPTION OF THE PREFERRED EMBODIMENTS

As indicated, the Applicant's invention resides in the fact that the perfluoroalkane sulfonamide is formed by reacting a perfluoroalkane sulfonylfluoride with an amine, according to well known reaction conditions, in the presence of finely divided silica. It is well known that silicic acid exists in many forms thus, for purposes of simplicity, 1 mole of $SiO_2$ is considered to be a mole of silica to which the quantities of initial materials utilized in the present invention are referred within the framework of the present invention.

The silica which is utilized preferably has a surface area between about 20 $m^2/g$ to about 600 $m^2/g$, most preferably from about 50 $m^2/g$ to about 450 $m^2/g$. The surface area is not critical, however, generally, it is usually not enough to simply grind quartz and then to utilize it in such a form in the practice of the present invention. Still, it is possible to prepare a silica with adequate surface areas by means of additional processing methods, such as dissolving and precipitating.

There are many known commercial products that have usable surface areas from about 50 to about 450 $m^2/g$. Commercially available products such as those utilized as fillers or pigments may be employed as the silica within the framework of the present invention. They typically have an adequately fine division, thus a suitably large surface area.

The silica utilized in the present invention may be dehydrated in a customary manner, such as by simply drying in a drying chamber at elevated temperature. It is, however, preferable to remove the water from the silica by means of azeotropic distillation, such as with the aid of toluene.

In general, the improved reaction of the present invention is carried out in the presence of at least about 1 mole of silicon dioxide per mole of sulfonylfluoride. Preferably, use is made of from about 2 to about 4 moles of silicon dioxide per mole of perfluoroalkane sulfonylfluoride. Most preferably, the silica is utilized in the form of dehydrated silica.

Again, it is usually preferable to perform the reaction between the perfluoroalkane sulfonylfluoride and the amine in the presence of a solvent. For such purposes, aprotic solvents, such as dioxane or aliphatic hydrocarbons, such as petroleum ether, or aromatic compounds, such as benzene, toluene or xylene, are especially well suited.

The molar ratio of amine to sulfonylfluoride, which is utilized as initial reactants, may vary within a relatively wide range, but generally about 1:1. Preferably, the ratio of amine to sulfonylfluoride is greater than 1, such as from about 1.1:1 to about 2:1.

The reaction conditions are well known and reference may be made to any of the aforementioned patents concerning reaction of perfluoroalkane sulfonylfluorides with amines. The reaction may, for example, be carried out at various temperatures, including elevated temperatures. However, for the sake of expedience, the reaction is typically carried out at room temperature.

The perfluoroalkane sulfonylflurides which are utilized in the practice of the present invention may be any such sulfonylfluoride e.g. with 1 to 14 carbon atoms which reacts with an amine to form a perfluoroalkane sulfonamide. Typically, the perfluoroalkane sulfonylfluoride compounds have the formula: $C_nF_{2n+1}SO_2F$, wherein n is an integer from about 4 to about 12.

The amines which are useful in the present invention are amines which are capable of reacting with the corresponding perfluoroalkane sulfonylfluoride to form the desired perfluoroalkane sulfonamide. Typically, the amine will be either a primary or secondary amine. The amine may, of course, be a mono-, di-, or polyamine so long as there is at least one reactive primary or secondary amine function. The usual amines will be mono-primary amines and mono-secondary/mono-tertiary diamines. Examples of such amines are butylamine, 1-amino-2-diethyl aminoethane, 1-amino-3-dimethyl aminopropane.

It was especially surprising that the process pursuant to the present invention permits the preparation of perfluoroalkane sulfonamides with high yields. It is not necessary to employ the amine in considerable molar excess to obtain an approximately quantitative conversion of the sulfonylfluoride to perfluoroalkane sulfonamides.

The hydrofluoric acid formed during the reaction is bonded quantitatively to the silica utilized. As a result it is possible to perform the reaction in all customarily utilized reacton vessels, since the hydrofluoric acid formed in situ is not capable of attacking the material due to the fact that it is bonded to the silica.

The crude reaction product may be processed by relatively simple methods and the degree of purity of the resulting product is excellent. Because of the high purity, the perfluoroalkane sulfonamides prepared pursuant to the present invention are especially well suited as valuable initial products in the preparation of surface-active substances.

As the hydrofluoric acid is bonded quantitatively by the silica, the hydrofluoric acid does not present any environmental problems, the presence of hydrofluoric acid or fluoride cannot be found in either the solvents utilized or in the end product, by means of calcium compounds. Thus, there is no danger that fluorine compounds will get into the waste water when the solvents are processed. Furthermore, reclamation of the solvents has become much simpler.

Removal, storage, and, if necessary, processing of the silica containing the hydrofluoric acid does not present any problems to one skilled in the art. Further details containing the present invention may be found in the following non-limiting examples. In the examples, the content of amine functions, if present in the reaction product, is determined by titration with perchloric acid in glacial acetic acid, making use of crystal violet as the indicator.

EXAMPLE 1

6.0 g of precipitated, commercially available silica, 60 ml toluene and 11.2 g (0.11 mol) N,N-dimethyl-propanediamine-(1.3) are placed in a vessel equipped with a stirrer, thermometer and a reflux condenser. 0.1 mol perfluorooctane sulfonyl fluoride is added by means of a droping funnel and the temperature rises to 70° C. The reaction product accumulates as precipitate and stirring is continued for 2 hours, at 60° to 70° C. The reaction mixture is then cooled to room temperature, and the reaction product and silica are filtered off. Only 0.3 g of the sulfonamide are left in the filtrate; it is not possible to detect hydrofluoric acid in the filtrate by means of alcoholic calcium chloride.

The filter cake is extracted with alcohol in a Soxhlet apparatus. After evaporation of the alcohol, 55.8 g (95.5% of theoretical) of the product are isolated. The extracted, dried residue weighs 8.12 g (theoretical value 8 g). An analysis showed 23.44% fluorine (theoretical value 23.39%). Using alcoholic calcium chloride solution, fluoride ion can likewise no longer be detected in an alcoholic solution of the end product. Titration with perchloric acid shows 68.9% perfluorosulfonamidopropyl dimethylamine.

EXAMPLE 2

6 g precipitated silica are mixed with 60 ml toluene and the water contained in the silica is removed with the solvent by means of azeotropic distillation. The process then proceeds as in Example 1, with the difference that the temperature is held at 20° by means of cooling and that the subsequent stirring for 2 hours is carried out at room temperature.

After processing as in Example 1, the resulting product amounts to 99% of theoretical. Titration with perchloric acid showed 90.3% perfluorooctanesulfamidopropyl dimethylamine.

Examples 3 to 8, which are compiled in the Table, were carried out in a manner similar to Example 1.

Table

| Example No. | Reaction temperature | Total yield | Titratable base content | Remarks |
|---|---|---|---|---|
| 3 | 60 | 98.7 | 61.5 | dioxane solvent |
| 4 | 20 | 87.5 | 77.8 | amine metered into sulfonyl-fluoride |
| 5 | 20 | 99 | 90.3 | |
| 6 | 65–70 | 75.7 | ./. | butylamine |
| 7 | 65–70 | 99.3 | 74.0 | 1-amino-2-diethyl aminoethane |
| 8 | 65–70 | 96.5 | 71.5 | 1-amino-2-diethyl aminobutane |

What is claimed is:

1. In an improved process for preparing perfluoroalkane sulfonamides by reacting a perfluoroalkane sulfonylfluoride with an amine, the improvement comprising performing the reaction in the presence of at least about 1 mole finely divided silica having a surface area from about 20 m²/g to about 600 m²/g, per mole of sulfonylfluoride.

2. The improved process of claim 1 wherein the molar ratio of amine to sulfonylfluoride is from about 1:1 to about 2:1.

3. The improved process of claim 1 or 2 wherein the perfluoroalkane sulfonylfluoride is reacted with an amine in the presence of a solvent.

4. The improved process of claim 3 wherein the solvent is an aprotic solvent.

5. The improved process of claim 3 wherein the solvent is toluene.

6. The improved process of claim 1 or 2 wherein from about 2 to about 4 moles of silica per mole of sulfonylfluoride is utilized.

7. The improved process of claim 3 wherein from about 2 to about 4 moles of silica per mole of sulfonylfluoride is utilized.

8. The improved process of claim 1 or 2 wherein the silica is dehydrated silica.

9. The improved process of claim 3 wherein the reaction is performed at room temperature.

* * * * *